United States Patent
Haugholt et al.

(10) Patent No.: US 7,633,614 B2
(45) Date of Patent: Dec. 15, 2009

(54) DEVICE AND A METHOD FOR DETECTION OF CHARACTERISTIC FEATURES OF A MEDIUM

(75) Inventors: Karl Henrik Haugholt, Oslo (NO); Svein T. Idsøe, Oslo (NO); Anders Eikenes, Bekkestua (NO)

(73) Assignee: Tomra Systems ASA, Asker (NO)

( * ) Notice: Subject to any disclaimer, the term of this patent is extended or adjusted under 35 U.S.C. 154(b) by 464 days.

(21) Appl. No.: 11/575,634

(22) PCT Filed: Sep. 23, 2005

(86) PCT No.: PCT/NO2005/000351

§ 371 (c)(1),
(2), (4) Date: Mar. 20, 2007

(87) PCT Pub. No.: WO2006/041303

PCT Pub. Date: Apr. 20, 2006

(65) Prior Publication Data

US 2007/0296956 A1      Dec. 27, 2007

(30) Foreign Application Priority Data

Sep. 24, 2004   (NO) .................................. 20044061

(51) Int. Cl.
*G01N 21/00* (2006.01)
(52) U.S. Cl. ............... 356/239.4; 356/239.6; 356/240.1
(58) Field of Classification Search ............... 356/239.1, 356/239.4, 239.5, 239.6, 240.1, 432
See application file for complete search history.

(56) References Cited

U.S. PATENT DOCUMENTS

| | | | | |
|---|---|---|---|---|
| 3,723,731 A | * | 3/1973 | Blau, Jr. ..................... | 356/451 |
| 4,551,022 A | * | 11/1985 | Tagaya ........................ | 356/406 |
| 4,885,709 A | * | 12/1989 | Edgar et al. .................... | 702/30 |
| 5,141,110 A | * | 8/1992 | Trischan et al. .............. | 209/524 |
| 5,403,433 A | * | 4/1995 | Morrison et al. .............. | 216/60 |
| 5,436,722 A | * | 7/1995 | Baldwin .................. | 356/239.4 |
| 5,539,514 A | | 7/1996 | Shishido et al. | |
| 5,794,788 A | | 8/1998 | Massen | |
| 6,497,324 B1 | | 12/2002 | Doak et al. | |
| 2003/0053050 A1 | * | 3/2003 | Potyrailo et al. ............ | 356/326 |
| 2004/0263850 A1 | * | 12/2004 | Li et al. ....................... | 356/432 |

FOREIGN PATENT DOCUMENTS

DE        10018940 A1    10/2001

(Continued)

*Primary Examiner*—Roy Punnoose
(74) *Attorney, Agent, or Firm*—Rodman & Rodman

(57) ABSTRACT

A device and a method for detection of characteristic features of a medium that is wholly or partly transparent, wherein said medium is placeable in an observation area in a light path extending between a light source and a light detector, wherein said medium is illuminated by the light source in the observation area, wherein at least one light-directing optical element is arranged in connection with the observation area. Light transmitted through said medium, which is deflected by said medium when it is in said area and thus causes a change of light direction in said area, is detected. Characteristics of said medium are determined by spectrometry of the received light-deflected light, and a wavelength-sensitive element is used at a position in the light path, either at or as a part of the light source or the light detector.

76 Claims, 10 Drawing Sheets

FOREIGN PATENT DOCUMENTS

| | | | |
|---|---|---|---|
| EP | 1300200 | A1 | 9/2003 |
| FR | 2798995 | A1 | 3/2001 |
| GB | 1078181 | A | 8/1967 |
| GB | 1298658 | A | 12/1972 |
| GB | 2212261 | A | 7/1989 |
| WO | 9606689 | A2 | 3/1996 |
| WO | 9746329 | A1 | 12/1997 |
| WO | WO 0057160 | A2 | 9/2000 |
| WO | 03061858 | A1 | 7/2003 |
| WO | 2004016362 | A1 | 2/2004 |
| WO | 2004080615 | A2 | 9/2004 |

* cited by examiner

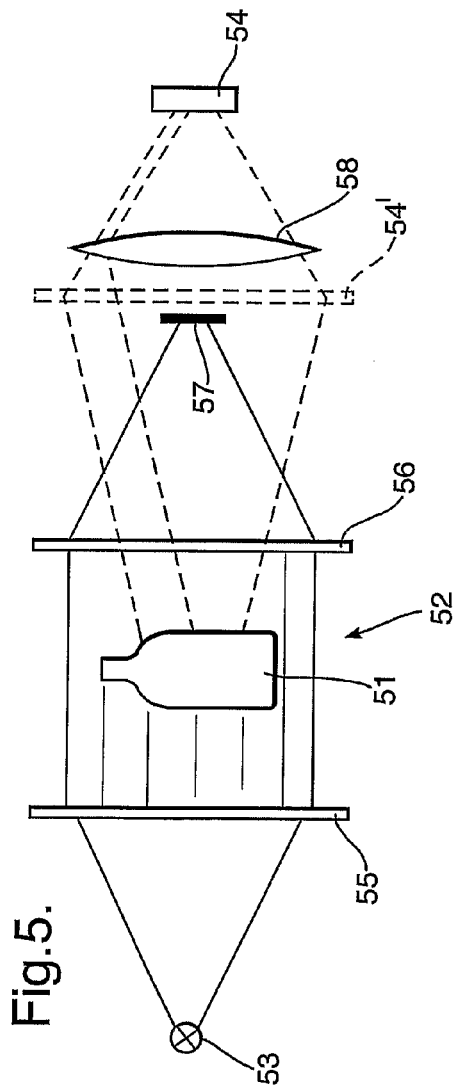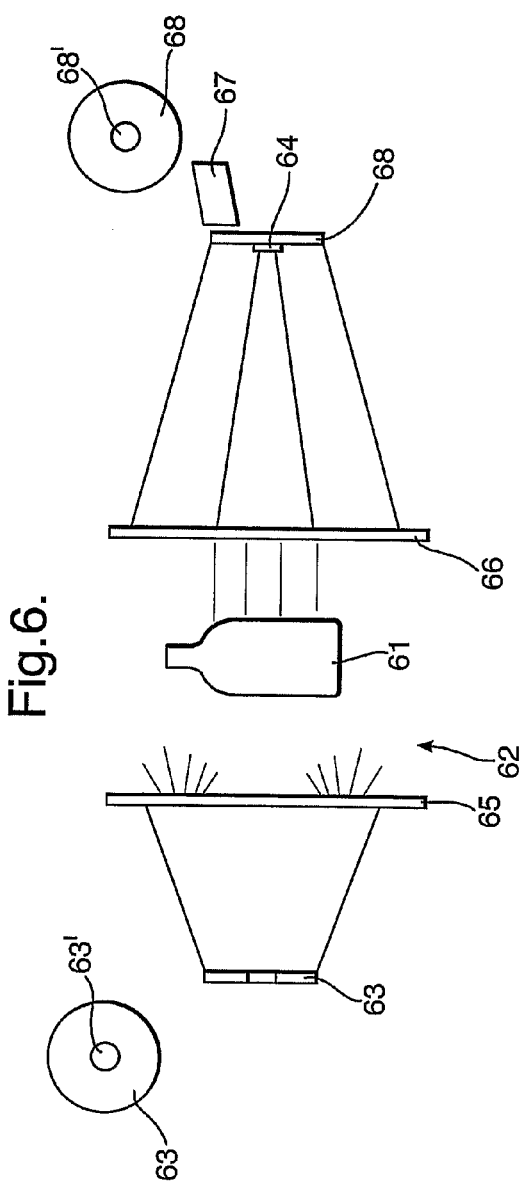

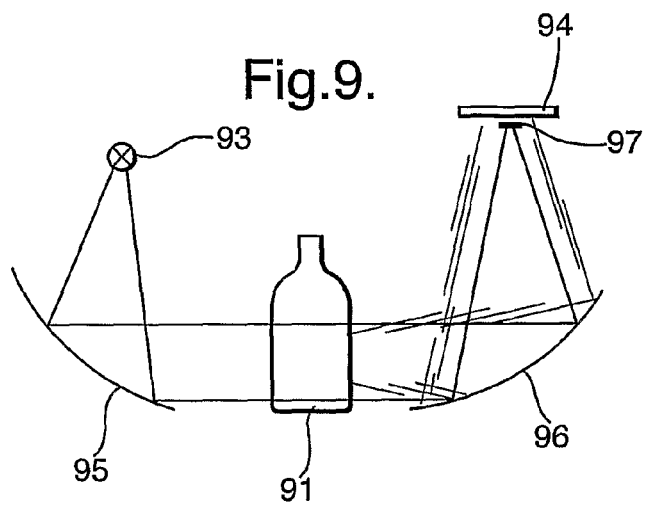
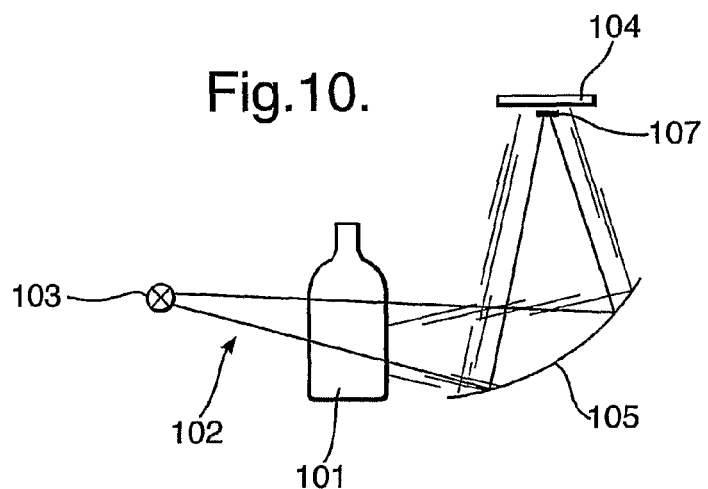
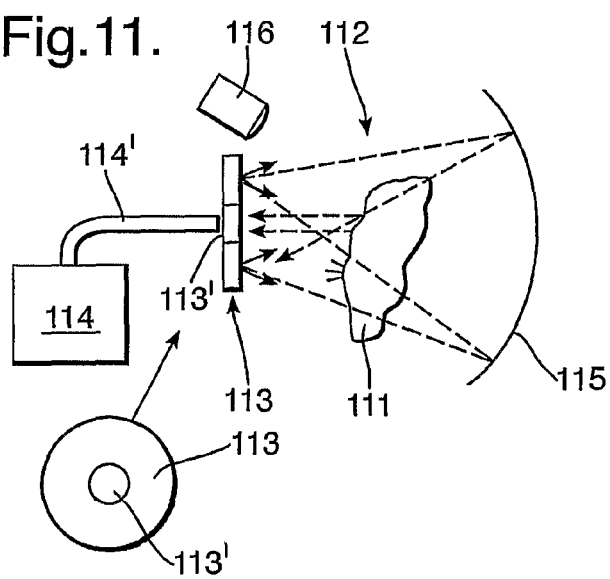

DEVICE AND A METHOD FOR DETECTION OF CHARACTERISTIC FEATURES OF A MEDIUM

BACKGROND OF THE INVENTION

The present invention relates to a device and a method for detection of characteristic features of a medium that is wholly or partly transparent, wherein said medium is placeable in an observation area in a light path extending between a light source and a light detector, wherein said medium is illuminated by the light source in the observation area, wherein at least one light-directing element is arranged in connection with the observation area, and wherein the light detector is adapted for determination of characteristics of said medium.

It is previously known to detect characteristic features of a medium, as for instance a physical article such as a bottle, by illuminating such an article with a light source via an optical element such as a lens and, on the opposite side, capturing any light that is not blocked by said medium so as to observe the contour of said article.

Recognition of the material type of the article is possible by means of known methods, as for instance successive transillumination of filters in a rotating filter wheel with typical material samples or narrow-band optical interference filters; diffraction of the light on an optical grating, and detection using a detector array; diffraction of the light on an angle scanning optical grating, and detection using a single light detector; and use of a wavelength-adjustable light source.

These known solutions require the detection area to be relatively narrow, otherwise the signal from the article will drown in the background signal. The article must thus be positioned inside the detection area or the detection area must be directed towards the article or medium. In this connection, reference is made, inter alia, to U.S. Pat. No. 5,794,788.

For further illustration of the prior art, reference is made to U.S. Pat. No. 6,497,324 and WO-A2-2004/080615. U.S. Pat. No. 6,497,324 is based on a technique which primarily makes use of reflected light. If the article is transparent or clear, a second portion of incident light will be transmitted through the article, hit a retro-reflector, reflect off the reflector, and then pass back through the article and to a collector. This method is referred to as "transflection" and is used to determine frequencies of electromagnetic radiation in the IR spectrum reflected by the article. The main purpose of the retro-reflector is related to calibration uses. WO-A2-2004/080615 relates to the detection of reflected light.

Other known solutions consist of scanning the field of view of the detector above the detection area, thereby obtaining a good signal/noise ratio when the field of view hits the article. Other known technology is to use an NIR/IR camera to image a detection area. Furthermore, the objects can be forced mechanically into particular positions (which can easily be reached with an optical scanner), and a scan can be carried out along these positions using movable mirrors or movable optical fibres. In this connection, reference is made to EP Patent 0776257 and International Patent Application, Publ. No. WO 00/57160.

To make an inexpensive solution, an attempt could be made to avoid mechanical scanning, to avoid forcing the object past the sensor area, or to avoid choosing costly NIR/IR camera solutions. Instead a large detection area could be illuminated, and a signal detected from the whole of this area. Small objects would then drown in the signal/background signal, with the result that the recognition result would be inadequate for these objects.

Clearly, therefore, these solutions have their operative limitations.

However, the object of the present invention is to remedy these deficiencies of the known solutions, in particular with a view to being able not only to detect large but also small articles/objects in a reliable way, and in such manner that if there is no article or object in the measuring volume, there will be no signal from the detector either.

SUMMARY OF THE INVENTION

According to the invention, the device is characterised in that the detector is adapted to only capture light transmitted through said medium which is deflected by said medium when it is in said area and thus changes direction in the area, and that at least one wavelength-selective element related to the operation of the light source or the detector is placed in the light path from the light source to the detector.

According to the invention, the method is characterised by detecting only light transmitted through said medium which is deflected by said medium when it is in said area and thus causes a change of direction in said area, determining the characteristics of said medium by spectrometry of the deflected light received by the light detector, and using a wavelength-selective element at a position in the light path, the element being related to the operation of the light source or the detector.

These features and other embodiments will be set forth both in the attached patent claims and in the following description with reference to the attached drawing figures, these drawing figures with accompanying description merely serving to illustrate typical, but non-limiting embodiments of the invention.

BRIEF DESCRIPTION OF THE DRAWINGS

FIG. 5 shows a fifth embodiment of the device according to the invention.

FIG. 6 shows a sixth embodiment of the device according to the invention.

FIG. 9 shows a ninth embodiment of the device according to the invention.

FIG. 10 shows a tenth embodiment of the device according to the invention.

FIG. 11 shows an eleventh embodiment of the device according to the invention.

DETAILED DESCRIPTION OF THE INVENTION

As mentioned above, the object of the invention is to provide a device and associated method for the purpose of detecting characteristic features of a medium that is wholly or partly transparent. Such a medium may be in solid or liquid form.

If the said medium is in a solid form it may typically be a physical article, as for instance made of a material of glass or plastic. One particular use could be, e.g., to detect the material type of empty packaging such as bottles or cans of glass or plastic.

It is also possible to use the invention in connection with the detection of substances that are present in a liquid medium, e.g., waste water components, which in a duct can, e.g., pass by observation windows in the observation area.

Furthermore, the invention can be used in the detection of gas leaks. It is previously known that so-called "Schlieren" photography can be used to detect gas leaks, wherein images are taken of only the light that changes direction because of light scattering in a moving gas. The method may be suitable for detecting/monitoring large volumes, but it is not possible to assess the spectral composition of the gas and thus assess the type of gas and the concentration of the gas.

It is also known that IR-spectroscopy can be used to detect gas leaks in a limited measuring volume. When measuring large volumes, it will however be difficult to obtain a sufficiently large signal/background ratio to ensure adequate detection of the gas, especially if it is desirable to detect low gas concentrations.

By means of the present invention it is possible to ensure that only light which changes direction because of interaction with the gas reaches the detector. Thus, the signal/background ratio will increase considerably. In addition, traditional "Schlieren" photography with a digital camera can also be used so as to see where in the detection volume the leak originates from.

For the sake of simplicity, the present invention will now specifically be described, although merely by way of example, in connection with the detection of characteristic features of a medium as, for instance, a bottle of glass or plastic.

Figure 1:
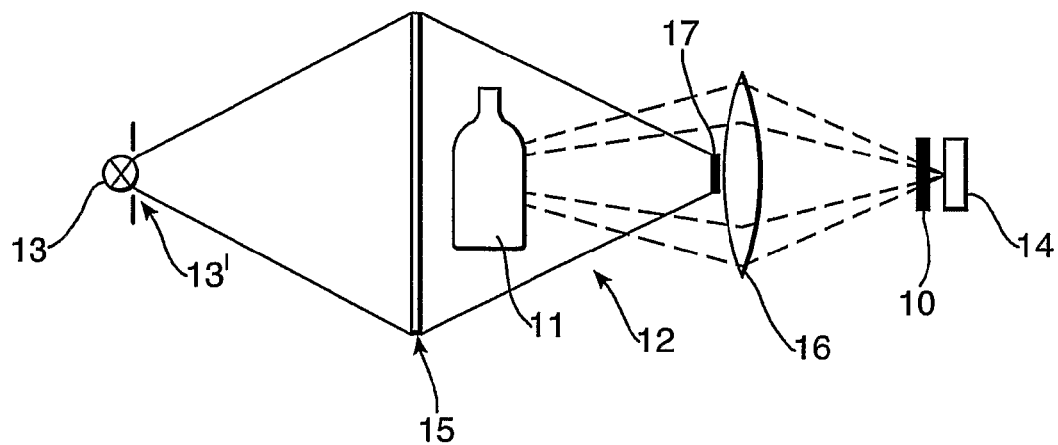
FIG. 1 shows a first embodiment of the device according to the invention.

As mentioned above, in particular in connection with FIG. 1, the said medium, in this case, for example, a bottle 11, can be placed in an observation area 12 in a light path extending between a light source 13 and a light detector 14, wherein said medium 11 is illuminated by the light source in the observation area, and wherein at least one optical focusing element 15 is arranged in connection with the observation area. FIG. 1 shows two optical focusing elements 15, 16.

The detector 4 is adapted to only capture light transmitted through said medium, in this case through the bottle, which is deflected by said medium when it is in said area and thus changes direction in the area. This is one of the basic principles of the invention. Furthermore, it will be understood that the light detector 14 is adapted for determination of characteristics of said medium, e.g., the material type. As the invention is based on a spectral consideration of the light that is captured, it is desirable that at least one wavelength-selective element is placed in a light path extending from the light source to the detector. The spectral consideration will allow a comparison to be made with, e.g., stored data, so as to determine desired characteristics of said medium.

It may be expedient that the wavelength-selective element is in fact constituted by or arranged in direct connection with the light source. In such a case, it is conceivable that the light source may be, e.g., a tunable laser or a modulatable light-emitting diode. As an alternative, it is also possible that the wavelength-selective element is arranged within or in connection with the detector itself.

The wavelength-selective element, whether it is integral with the light source or the light detector, or is in connection with one of these, will typically operate in the infrared spectrum or near-infrared spectral range (NIR).

Although in the above and merely by way of example, the focus is on allowing said characteristics to be typically represented by the material or substance type of said medium, or, e.g., the composition of materials or substances, such as in waste water or where a product consists of several materials, e.g., integrally cast, it is also possible within the scope of the invention that said characteristics may be related to properties of said medium, such as one or more of: temperature, pressure, viscosity, contamination, rate of motion, density, and change of state, e.g., related to a given reference.

When detecting a solid medium, e.g., physical articles, but also a liquid medium, the said medium will be surrounded or "supported" by a fluid, e.g., air, gas or liquid in the observation area. A surrounding or supporting fluid of this kind should have characteristic light deflecting properties that are different from the light deflecting properties of the aforementioned medium.

Figure 3:
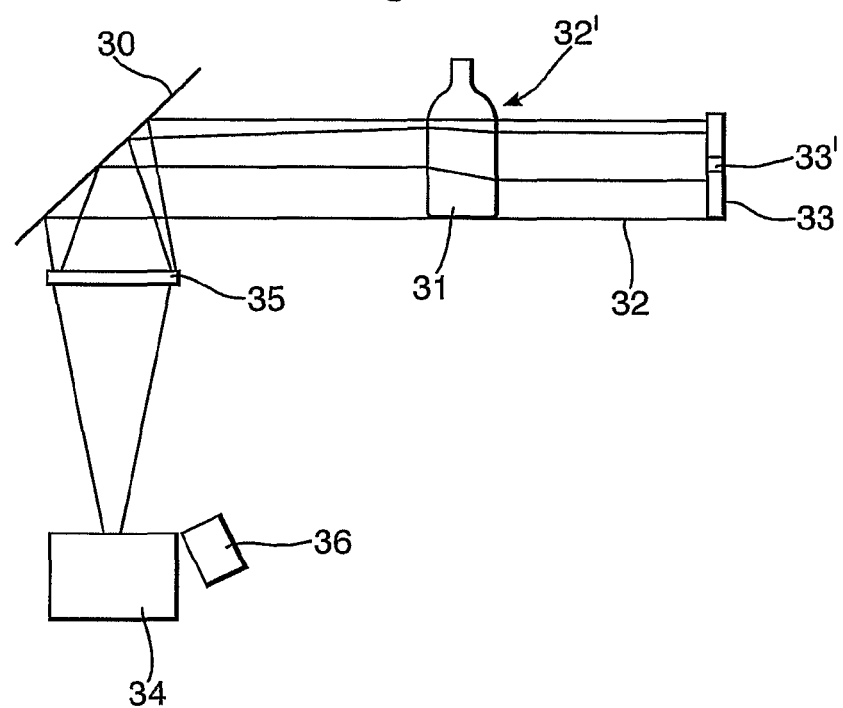
FIG. 3 shows a third embodiment of the device according to the invention.

As is typically shown in FIG. 3, but which per se is also conceivable for the other described embodiments, e.g., in FIG. 1, it is possible that the observation area 32 for said medium 31, when seen in the light path from the light source 33 to the detector 34, is located before the first occurrence of said at least one optical element 35. In FIG. 3 it can also be seen that the device can be compressed using a deflecting mirror 30.

It is also shown in, inter alia, FIG. 1, that the observation area 12 may be so situated in the light path from the light source 13 to the detector 14, that it is located after the first occurrence of the said at least one optical element. The same can also be seen, inter alia, in FIGS. 2, 4, 5, 6, 7, 8, 9 and 12, and also 16 and where said medium 21; 41; 51; 61; 71; 81; 91; 121; 161 is in the observation area 22; 42; 52; 62; 72; 82; 92; 122; 162.

As shown especially in FIGS. 1, 2, 4, 5, 6, 7, 9 and 12, and also in FIG. 16, a first focusing optical element 15; 25; 45; 55; 65; 75; 95; 125; 165 is located at a first position in the light path. A second focusing optical element 16; 26; 46; 56; 66; 76; 96; 126; 166 is located at a second position in the light path between the first position and a detector 14; 24; 44; 54; 64; 74; 94; 124; 164. As shown, the first element receives light from a light source 13; 23; 43; 53; 63; 73; 93; 123; 163 and directs this light on towards the second element, and light from the second element is directed towards the light detector. The medium to be detected is indicated by the reference numerals 11; 21; 41; 51; 61; 71; 91; 121; 161.

Figure 7:
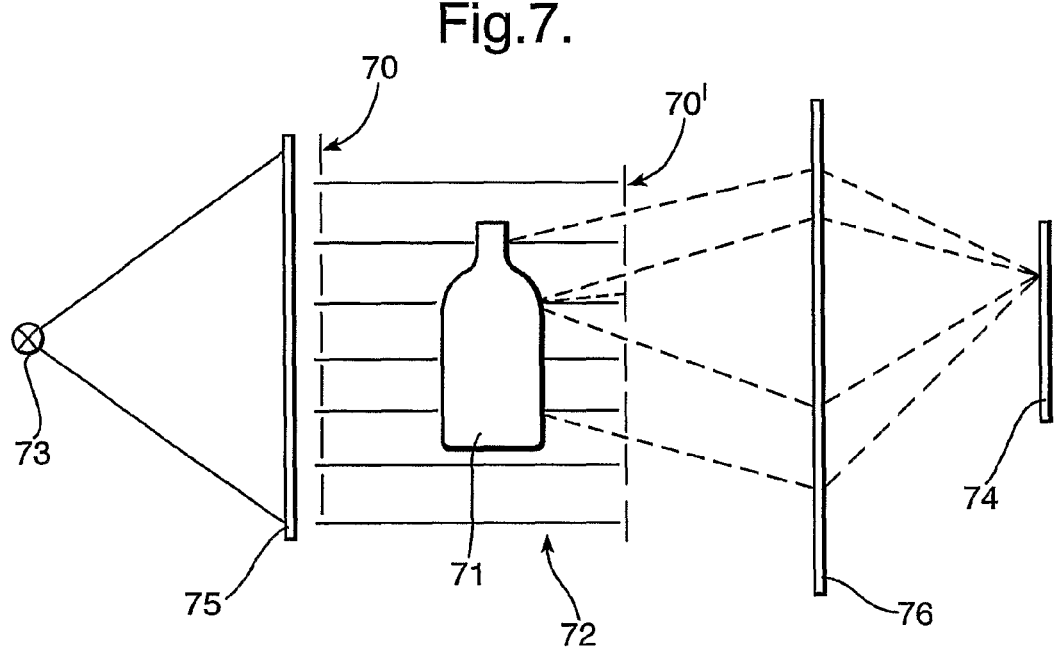
FIG. 7 shows a seventh embodiment of the device according to the invention.

In FIGS. 5, 7 and 9, the light that is directed from the first element towards the second element will be parallel light.

In a first optical path length between the second element and the detector there may be located a light stop 57, as shown in FIG. 5, to stop light which has not changed direction on passing through said observation area and which thus is focused towards the light stop. In a second optical path length located between the light stop 57 and the detector 54 there is located a converging lens 58 for focusing light that is deflected by said medium 51 in said observation area 52 and thus changes direction, and which is then led out from the second element 56 and passes outside the periphery of the light stop 57 towards the converging lens 58. However, it should be understood in connection with that shown in FIG. 5 that the converging lens 58 and the detector 54 could, if desired, be replaced by a light detector 54' with a substantially greater detection area than the detector 54.

In FIGS. 1, 2, 5, 7, 8, 9 and 10 it is indicated that the light source 13; 23; 53; 73; 83; 93; 103 is advantageously a point light source. FIG. 1 indicates that point light can, for example, be provided by passing the light through a diaphragm aperture 13'.

Figure 4:
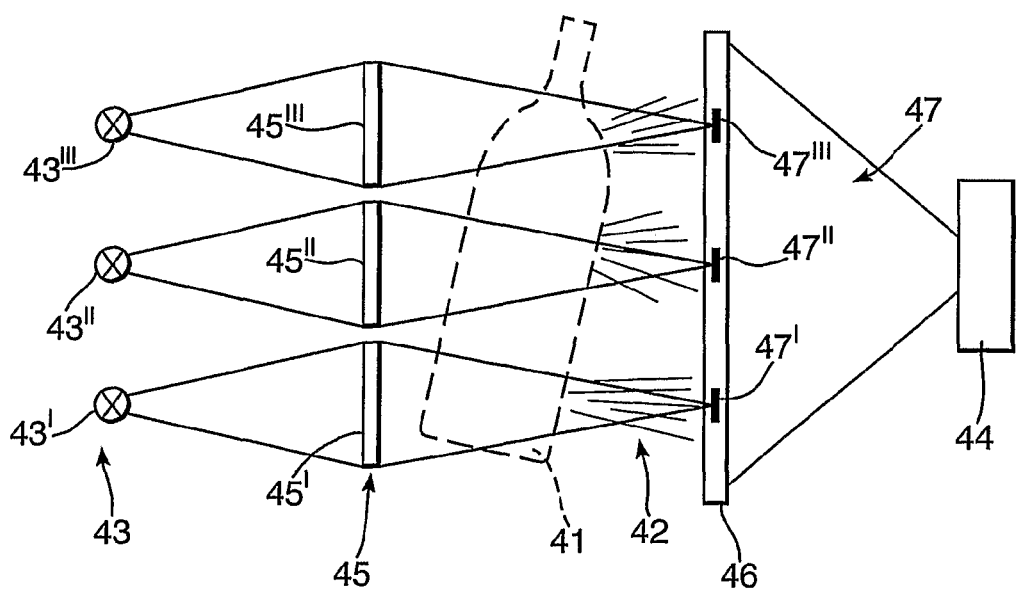
FIG. 4 shows a fourth embodiment of the device according to the invention.

FIG. 4 shows a special case that would be especially suitable for, e.g., detecting articles or a medium that has a length greater than what is "normal". Here, in the illustrated example there are three light sources 43', 43", 43''', generally designated as the light source 43, which send light towards an optical focusing element 45 which in this case is split into three sections 45', 45", 45'''. It will be seen that if medium 41, as for instance a bottle, is not present in the observation area 42, the light from each light source is directed towards respective light stops 47', 47", 47''' (generally designated 47). Only the light that is transmitted through said medium 41 will be focused via the optical focusing element 46 towards the detector 44.

Figure 2:
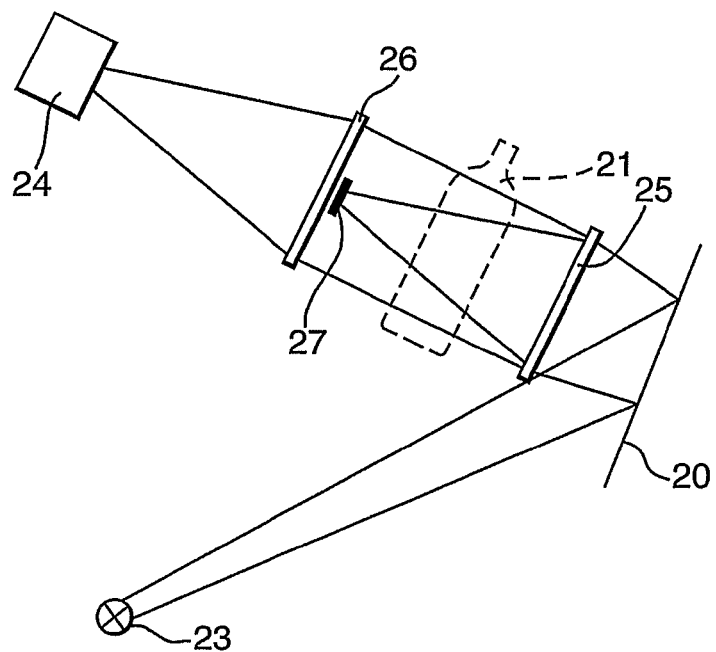
FIG. 2 shows a second embodiment of the device according to the invention.

In FIGS. 1 and 2 there is a simplified version of that shown in FIG. 4, where there is just one light source 13; 23 and where light that is not transmitted through said medium 11; 21 will be stopped by a light stop 17; 27, so that such light does not reach the detector 14; 24.

In FIG. 2 it will be seen that a light-deflecting element 20, such as, e.g., a plane mirror, has been placed in the light path between the light source and the first optical focusing element. The purpose of this is merely to allow the physical dimension of a device according to the invention to be reduced, and this method is per se known.

In FIGS. 3, 6, 11 and 12, and also 16, it will be seen that the light source 33; 63; 113; 123; 163 is a light source with a dark centre. Alternative solutions of a light source of this type are shown in FIGS. 13a, 13b and 13c. Such a light source with a dark centre 33'; 63'; 113'; 123'; 163' may be selected, e.g., from the group consisting of: an annular light source (FIG. 13a); a polygonal light source (FIG. 13b); a light source with a pair of parallel light lines (FIG. 13c); at least two light sources arranged as a frame or ring around said dark centre (FIGS. 13a and 13b); a reflector-based light source (FIG. 16).

In FIG. 6 it will be seen that the light source 63 and the first optical element 65 provide light in an intermediate area 62 which includes the observation area for said medium 61, i.e., between the first optical element 65 and the second optical element within a specific angularly dispersed spectrum, so that the light coming into the area 62 from the element 65 does not include forward-directed parallel light. The second element 66 is arranged to focus light from the intermediate area 62 towards an image plane 68 in order to generate on the plane an image 68, 68' of the light source 63 with its dark centre 63', and to focus light that is deflected by said medium on transmission of light therethrough in a forward direction as parallel light towards the second element 66 and from there focused onwards towards a light detection field for transmitted light represented by said dark centre, and where the light detector 64 as shown is located in this light detection field 68'.

A second, interesting embodiment can be seen from that shown in FIG. 7, where in an optical path area 72 between the first element 75 and the second element 76 there is located a first raster or chequerboard-like filter 70 to filter away part of the parallel light coming from the first element 75. In the optical path at the exit from said optical path area 72 there is located a second raster or chequerboard-like filter 70' which is offset relative to the first filter 70 so that parallel light which is allowed through by the first filter and is not deflected by said medium 71 on transmission of the light therethrough, when such a medium is located in said optical path area 72, is stopped by the second filter 70'. The second optical focusing element 76 is arranged to capture light that has been received by said medium, transmitted through it and deflected out therefrom towards and through the second filter 70'. The detector 74 is arranged to capture said transmitted, deflected light which comes focused from the second element 76 towards the light detector 74.

Figure 8:
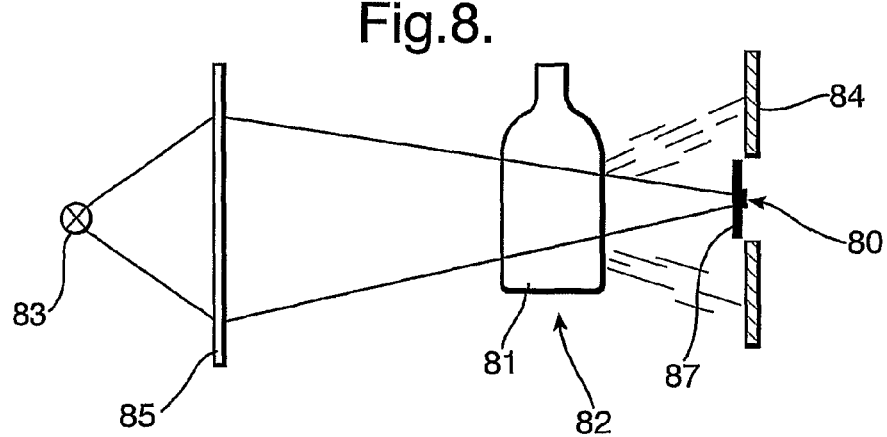
FIG. 8 shows an eighth embodiment of the device according to the invention.

In FIG. 8 it is shown that light is directed towards the first element 85 from a point light source 83 and is directed on from the first element towards a focusing point 80. In an optical path area close to the focusing point 80 there is located a light stop 87 adapted to stop that of the point light source generated light which has not changed direction on passing through the observation area 82 and which is focused towards the light stop 87. A light detector 84 is placed behind or around the light stop 87 for detecting the light transmitted through said medium 81 which is deflected by said medium in the detection area and changes direction so that it strikes the detector 84.

The embodiment shown in FIG. 9 is, in terms of function, quite similar to that shown and described in connection with FIG. 5. A light source 93, preferably a point light source, can be seen in FIG. 9. The light is sent towards a first optical focusing element 95 and passes from there as parallel light to a second optical focusing element 96, from where the light is focused towards a light stop 97 which is in front of the light detector 94 or is surrounded thereby.

This means that it is only light that is transmitted through said medium 91 and deflected thereby which in turn will strike the detector 94.

A simplified version of that shown in FIG. 9 is shown in FIG. 10. The solution in this figure is functionally quite similar to that shown in FIG. 8, although the observation area 102' for said medium 101' in this case is between the light source 103 and the optical focusing element 105. Like the light stop 87, there is in this case a light stop 107. When there is no medium in the light path between the light source 103 and the detector 104, the light coming from the light source will be focused towards the light stop 107. It is therefore, as described above, only the light that is transmitted through and deflected by the said medium 101' that will be able to pass via the element 105 and hit the detector 104. The detector 104 is either placed behind the light stop 107 or is located around the periphery thereof.

Figure 12:
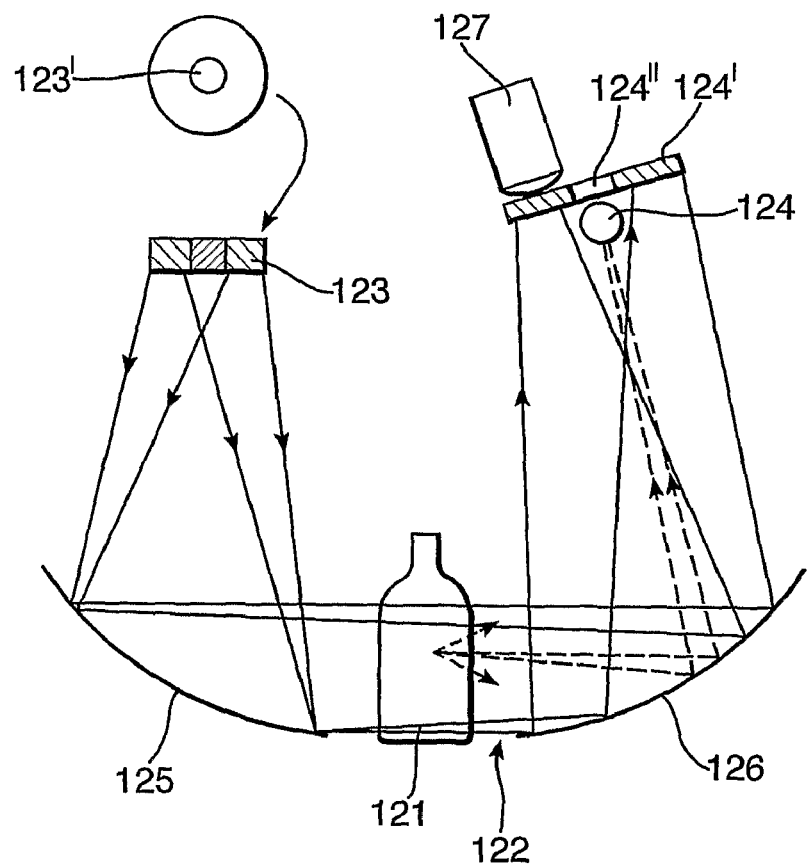
FIG. 12 shows a twelfth embodiment of the device according to the invention.
Figure 13A:
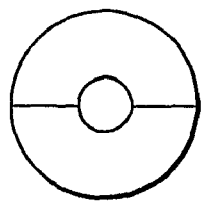
FIG. 13 shows alternative embodiments of light sources with a dark centre.
Figure 13B:
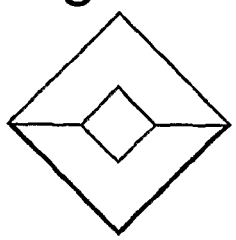
Figure 13C:
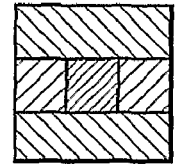

FIGS. 11 and 12, and also FIG. 16, show a first optical focusing element 115; 125; 165 which receives light from a light source 113; 123; 163 that has a dark centre 113'; 123'; 163' and directs this light on towards the light detector 114; 124; 164.

As shown in FIG. 11, both the light source 113 and the first element 115 will in reality provide light in an intermediate area 112 which serves as observation area for observing the medium 111 which may be located between the first element 115 and a light detector 114, and where the light in within a specific angularly dispersed spectrum which does not include light focused in towards the light detector 114. The first element 115 is arranged to focus light towards an image plane located in the same or roughly the same plane as the light source 113 in order to generate an image of the light source with its dark centre given by reflection back off the first element 115, and the light detector 114 is placed in said image plane coaxial with the dark centre 113' of the light source, optionally with assistance of a light guide 114', in such manner that at least a part of the light which on transmission through said medium is deflected by said medium in a direction towards a light detection field, represented by said dark centre 113', will hit the light detector 114; 114' which is located in the light detection field.

In FIG. 11 a part of the light that reaches the detector 114 may come from a surface reflection on the object 111. If the object is not transparent, a large part of the light will originate from the surface reflection, and spectral analysis of this reflected light will provide information about the object's material type.

The first focusing optical element 115 in FIG. 11 is advantageously a spherical or ellipsoid reflector. Alternatively, the optical element 115 may have another, aspherical shape, for example, a paraboloid shape or hyperboloid shape.

Figure 14:
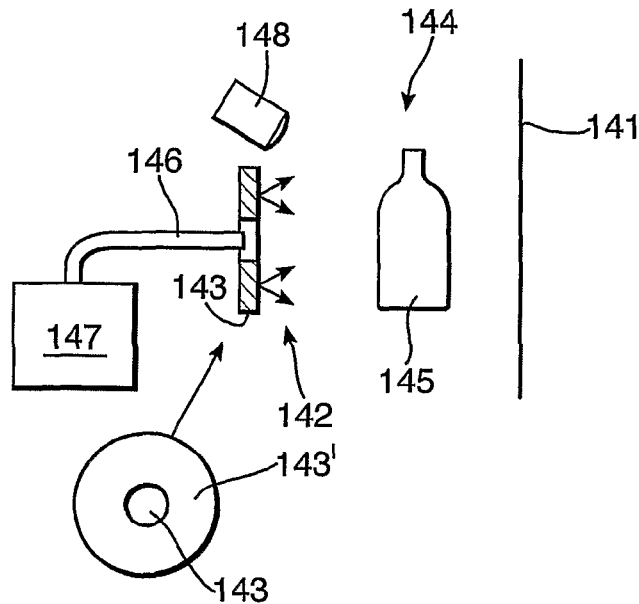
FIG. 14 shows a thirteenth embodiment as a variant of the embodiment shown in FIG. 11.

FIG. 14 shows a variant of FIG. 11 where the optical element 141 may be a retro-reflective surface. Light 142 from a light source 143 that strikes the surface 141 will initially be reflected back to the same point on the light source 143 from which it was sent. However, a retro-reflective surface of this kind will not always have a perfect structure, e.g., if it is formed of a reflective tape or reflective cloth. The retro-reflective surface 141 may be flat or curved. When no article is present in the detection area 144, the centre 143' of the light source 143 will be dark. When an article 145, such as a bottle, is present in the detection area 144, the light that arrives at the centre 143' will be directed via a light guide 146 to a detector 147, and such light will emanate from the article either as reflection from its surface, or as light transmitted and diffusely scattered through the article (in this case a bottle). In general, diffuse light scattering through the article (e.g., the bottle) will have the effect that the return light will always be scattered and therefore with at least a part thereof will hit the detection area and the light guide. If the light typically is only refracted, but not scattered through the article, this solution will nevertheless be useful with a retro-reflector, as a retro-reflector is often not perfectly retro-reflecting and therefore causes some light scattering when the light leaves the retro-reflector.

In FIG. 12 it can be seen that a light source 123 together with a first optical focusing element 125, located at a first position in the optical path, provides light in an intermediate area or observation area 122 between the first element 125 and a second optical focusing element 126. The second element 126 is arranged to focus light coming from the intermediate area towards an image plane 124' in order to generate on the plane an image of the light source 123 with its dark centre 123'. When a medium, e.g., an article 121, is in the observation area, the light transmitted through said medium and deflected thereby will pass in a forward direction towards the second element 126, and will be focused onwards from there to a light detection field 124" whose position is related to the position in which said dark centre 123' will appear if no medium 121 is in the area 122. A light detector 124 is arranged in the light detection field 124". Under "normal" circumstances, i.e., without any medium 121 to be detected, light which comes from the light source 123 will be imaged on the image plane 124' with said dark centre 123'. When said medium 121 enters the light path, light which is transmitted through it will be deflected, and will thus move away from the normal light path and be deflected into the focusing area which from the element 126 is directed towards the detector 124 in the light detection field 124" and which is located in the centre of the image plane 124'.

The light source 113; 123 with a dark centre could be of a type as previously shown and described; cf. for example, FIG. 13.

The detectors that are shown and described include advantageously an optical diffractive element with an entrance aperture to the detector configured to cause imaging on the diffractive element of at least a substantial part of the observation area. This optical diffractive element is not shown in detail in the drawing figures as a person skilled in the art will understand how such an element could be used in a chosen detector.

As indicated in FIG. 1, a light mixer or a light diffuser 10 may be arranged in connection with the light detector 14.

In the solutions shown in FIGS. 9-12 and FIG. 16, a single or double curved mirror is advantageously used as focusing optical element 95; 105; 115; 125; 165. In connection with the embodiments shown in FIGS. 9 and 12, at least one of said first and second elements 95, 96; 125, 126; 166 will be formed of a single or double curved mirror.

In a slightly different configuration as regards the light path direction, the first optical element may conceivably be formed of a lens or a lens segment. Referring again to FIGS. 9 and 12, at least one of said first and second elements could therefore be formed of a lens or a lens segment.

As shown and described in connection with FIG. 2 and FIG. 3, there can, as mentioned be placed in the light path between the light source and the detector at least one mirror element 20; 30 for redirecting the light path. This mirror may be a plane mirror and its sole purpose is to make the whole device physically less voluminous. The mirror element is advantageously placed in the light path between the light source and the first optical focusing element 25; 35, although it could have been placed further out in the light path, i.e., closer to the detector.

In the invention as described, an IR spectrometer is advantageously used as an example of a detector. It is possible to place a digital camera in combination with this detector, as for instance indicated in FIG. 12 by means of the reference numeral 127. The camera will be able to receive light from the same observation area as the rest of the optical measuring system, here represented by the detector 124. The camera image will be able to provide information about object shape, object colour, degree of transparency in the visible range, and whether the observation area contains one or more objects. Here, it will be understood that the image plane 124' may in fact be imaginary. The camera will thus observe a very small part of the light source. It is required that the area of the light source in the field of view of the camera should have a very homogeneous distribution of light, so that small vibrations in the optical system will have little effect on the image generated by the camera.

A camera 36; 67; 116; 127; 148 can advantageously be placed in a measuring system which has an annular light source; see, e.g., FIGS. 3, 6, 11, 12 and 14. The camera should then be placed in the light source image plane, as for instance for the camera 67 in the image plane 68 shown in FIG. 6 in a position that is illuminated even when there is no bottle present in the observation area. The camera will thus be able to record background images when there are no bottles present, and use these to keep a check on the state of the light source in the visible range (e.g., intensity and colour temperature). This information can also be extracted in the infrared range.

When a medium, e.g., an article such as a bottle, is introduced into the detection area, some of the direct, transmitted light will be absorbed or change direction. At the same time, light which otherwise would not have reached the camera will change direction so that it acquires an angle which causes it to hit the camera. Since this light is transmitted through the bottle, it will contain information about the colour of the bottle. The light intensity from the bottle is determined by the bottle's optical density in combination with the bottle's scattering properties. Basically, the bottle will appear as darker than the background. In normal use, the background image (empty detection area) will be subtracted, and the bottle's contour will thus emerge more clearly.

Sunlight or other unwanted light may illuminate the bottle whilst the measurements are being made. To prevent this representing a problem, diffuse, reflected sunlight from the bottle's surface should be much less than light transmitted through the bottle from the measuring system. A typical bottle of plastic or glass will have most of the scattered and/or transmitted light within a small angular spectrum. By configuring the light source so that the bottle receives only this angular spectrum, a system of optimal energy efficiency will be made, as there is little likelihood of light with larger angles reaching the detector. The distance from the centre of the light source to its periphery corresponds to the illumination angle of the bottle.

By adjusting the area and form of the light source in combination with the position of the camera, the scattering angles that the camera is to detect can be set. In this context, "scattering angle" means the angle between the incident ray and the emergent ray on the medium that is to be investigated, e.g., a bottle. There is an optical relation between the scattering angles that are detected, extraction of colour information from the bottle, contrast between the bottle and the background light, and light source intensity.

Furthermore, a single camera can be used in combination with mirrors to view the object from several angles at the same time, in addition to the angle described in the previous paragraph. However, this not shown in the drawings, but a person skilled in the art will understand how this can be done without any further details.

As will be understood from the above, the camera in cooperation with the rest of the device has the function not only of detecting colour of the object and colour in the light that is transmitted, but also of detecting whether several objects are present at the same time in the detection area, which is not acceptable.

Advantageously, the device can be combined with other detectors and measuring devices for, in special cases, detecting objects that cannot be accepted.

Figure 15:
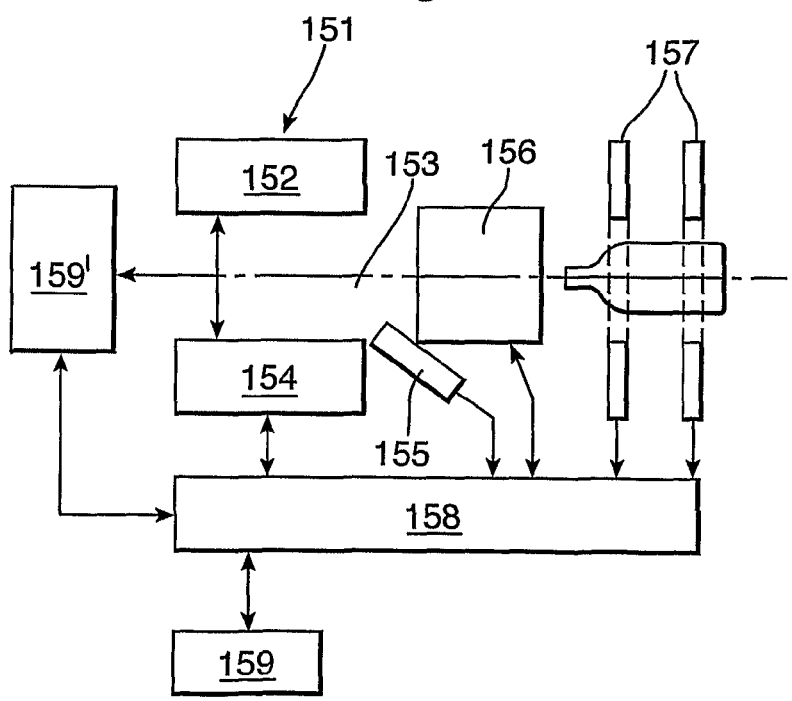
FIG. 15 shows a block diagram of the device according to the invention, wherein cooperating processor and additional detectors and measuring devices may be included.

FIG. 15 shows, in a highly simplified form, a device 151 according to the invention comprising light source 152, detection zone 153 and detector 154, according to the invention, in cooperation with camera 155, and other detectors and measuring devices, as, for instance, weighing instrument 156 and/or metal detector 157. A signal processing unit 158, such as a microprocessor, will be included and may be connected to peripheral equipment 159f, e.g., a display and printer unit, sorting device and or peripheral equipment 159", e.g., a compactor, disintegrator and/or material collecting bin for the medium or the object that is to be investigated.

In certain cases, soft drinks, for example, are supplied in standardised glass bottles on which is shrunk a stocking of a plastics material (e.g., PET), the stocking bearing information about the contents of the bottle. In such a case, a detection of the type of plastics material will be made, whilst a weighing instrument will detect that this is not a plastic bottle but a glass bottle covered with shrink-on plastic. Weighing and/or metal detection may also be of importance in case the bottle contains foreign objects, e.g. of metal.

Figure 16A:
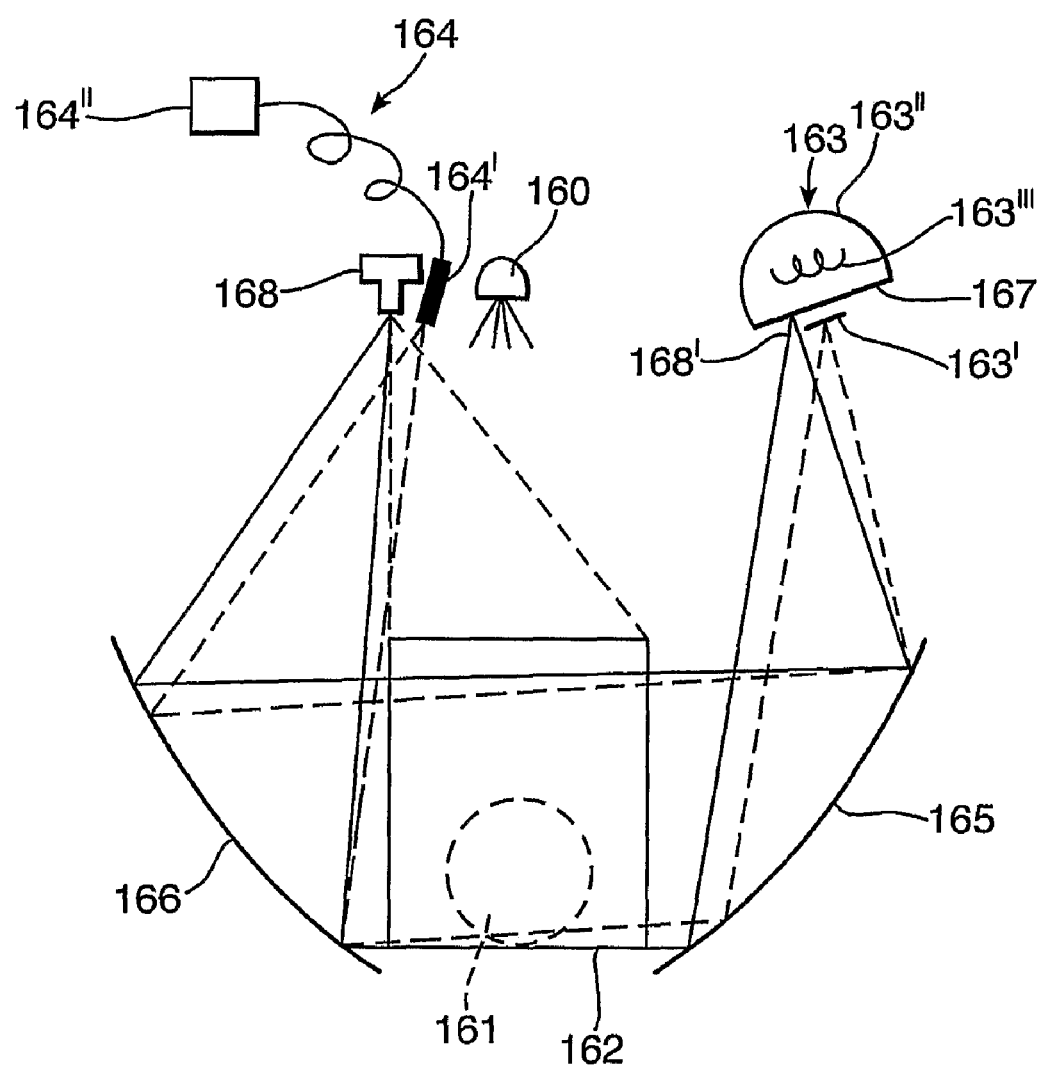
FIGS. 16a, 16b and 16c show a fourteenth embodiment of the device according to the invention, in respectively a front view, perspective view and top view (purely schematically).
Figure 16B:
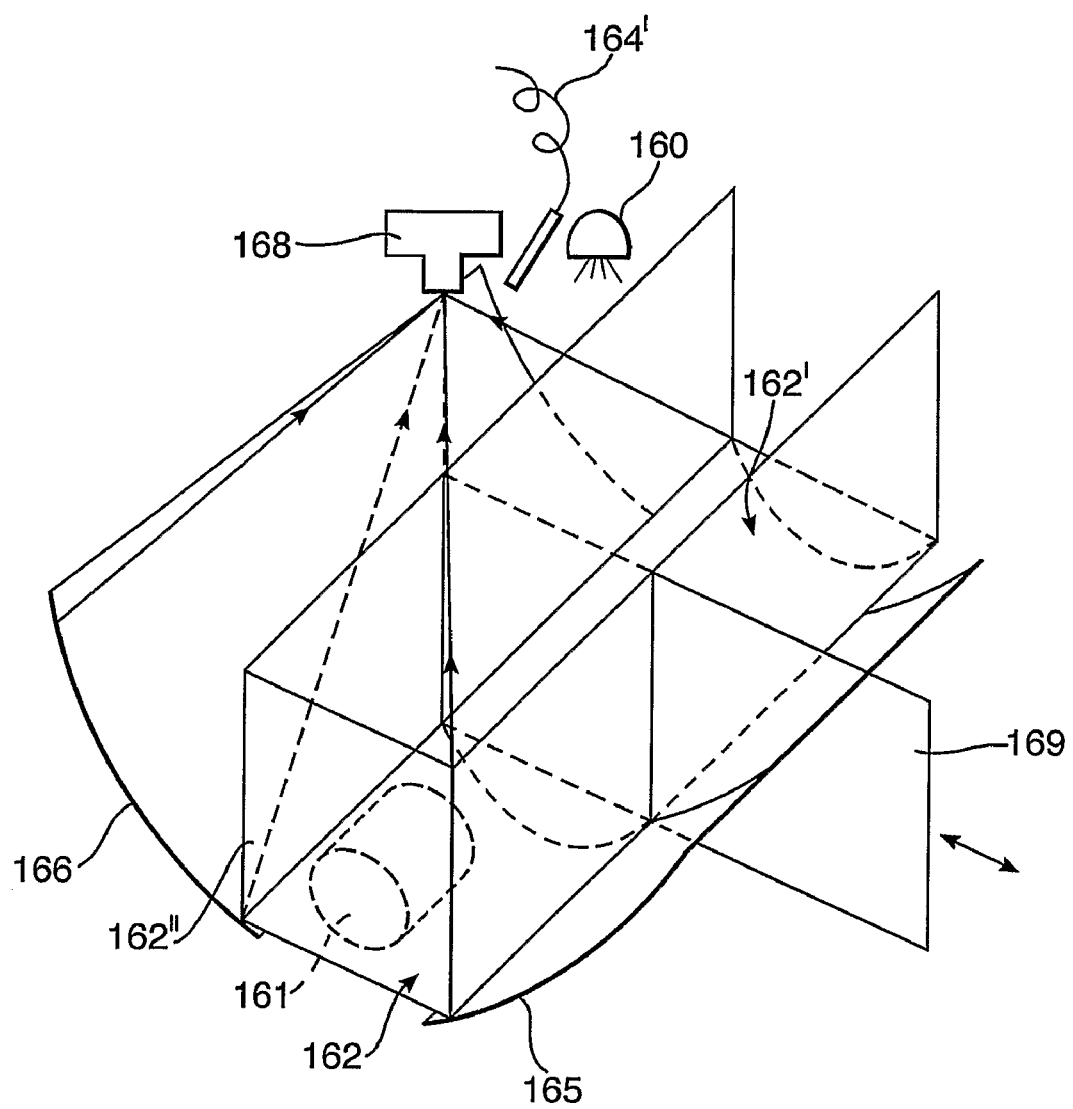
Figure 16C:
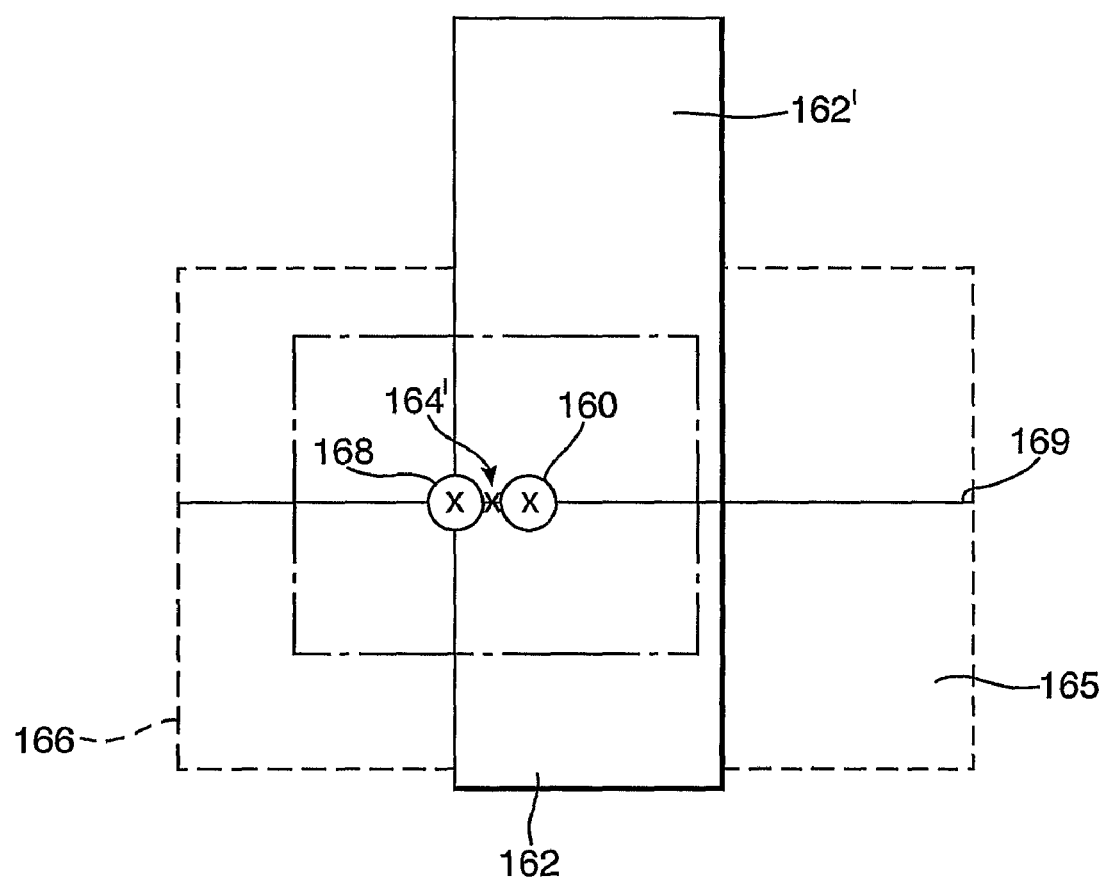

In the solution that is shown in FIGS. 16a-16c there is a light source 163 which has a dark diaphragm 163', and where the light source otherwise may, for example, consist of a reflector 163" with a lamp filament 163'". In connection with the light source 163, a light diffuser 167 may expediently be located between the reflector 162" and the diaphragm 163'. The diaphragm 163' is expediently mounted on the diffuser 167. The purpose of the reflector 163" is to be able to provide light for a side view of the medium 161, e.g., article, that is to be observed in an observation area or recognition chamber 162. Upstream of the chamber 162 there may be a receiving chamber 162'. A door device 169 is controllable to be opened and closed, and on opening to allow such medium 161 from the chamber 162' to enter the chamber 162. A camera 168 is located in proximity to the light detector 164. The camera's field of view is indicated by the reference numeral 168'. The light detector 164 consists expediently of an optical fibre 164' that conducts light to a spectrometer 164". An extra light source 160 is provided to be able to give top illumination of said medium 161, allowing it to be better viewed by the camera. The optical focusing elements 165 and 166 are preferably, but not necessarily, of the type off-axis, parabolic reflector.

In the solution shown in FIG. 16, the spectrometer 164" will receive light from said medium 161, e.g., a bottle, whilst it is inside the chamber 162. The camera 168 will view this medium from the side via the element 166, in addition to it merely viewing directly down into the chamber 162 from above, and in addition to also having an observation area related to the receiving chamber 162'. As will be seen from FIG. 16c, it will be important, if there is both a receiving chamber 162' and a recognition chamber 162, that the camera 168 is placed immediately above the door device, so that this shades neither the chamber 162' nor the chamber 162. The camera must also be placed immediately above the side walls of a recognition chamber 162, so that fastening ribs (not shown) holding a side wall window 162" belonging to the chamber do not shade the recognition chamber 162 or the side image viewed by the camera 168 via the element 166, The extra light source 160 is placed expediently as close to the camera as possible, so that the light source does not cast shadows on the bottom of the chamber 162 or 162'. Such shadows could otherwise easily result in the viewed area of the said medium or article being overestimated.

The focal points of the parabolic elements 165, 166 lie respectively in the dark diaphragm 163' and at the end of the optical fibre 164'. The recognition chamber 162 may advantageously be slightly tilted relative to the optical axis, so that the field of view of the spectrometer 164" does not include the bottom (the floor) of the chamber 162. The purpose of such tilting is to prevent diffusely scattered light from being produced by this floor, which could result in an increased amount of stray light into the spectrometer. Such stray light is not desirable.

The field of view 168' of the camera 168 on the diffuser 167 is only an area of some few $mm^2$. It is important that the diffuser 167 is as homogeneous as possible, so that any vibrations do not cause large intensity variations on the camera 168. The field of view 168' of the camera on the light source 163 should be between the dark diaphragm 163' and the periphery of the diffuser 167. Light that is scattered at a few degrees through said medium 161, e.g., a bottle, emanates from the area in proximity to this field of view. It is important that this area has adequate size and homogeneity. In other words, the diameter of the light source must be of such size that it is possible to observe the light scatter in, e.g., the range 0-6°. An angular range of this kind is sufficiently large for colour analysis of said medium to be adequate. A smaller angular range will produce dark areas on the articles that are too large to allow a colour analysis to be effective or possible.

With the described, camera-based side view observation of said medium's area, it will to some extent be possible to correct the signal provided by the spectrometer 164". The area of said medium that the camera views from above can be used together with a weight signal (e.g., from weighing instrument 156) to estimate said medium's (or article such as a bottle) density (i.e., weight per surface unit), and this area assessment can thus be included as a part of a material classification. Furthermore, the camera's side view of said medium will also cause there to be a reliable control of the door device 169, in addition to the material colour of a transparent medium. Such medium may optionally be an article, e.g., a bottle.

The camera's side view could conceivably be used to analyse the shape of an object, both to make material classification more effective and possibly to detect attempted fraud, several articles in one or both chambers, or other undesirable states of use.

The camera view from above could conceivably be used to carry out shape and/or movement analysis of articles, e.g., bottles, and also in that case it would be possible to detect attempted fraud, several articles in one or both chambers, or other undesirable state of use. The camera view from above also allows the material colour of an article to be assessed if it is not transparent. In addition, the view from above will make it possible to see whether any damage has occurred on functional parts of the chambers.

That described above in connection with the drawing figures is merely intended to serve as a non-limiting illustration of various aspects of the invention, as it will immediately be understood that also other embodiments of the invention could be envisaged within the scope of the invention as defined in the attached patent claims.

The invention claimed is:

1. A device for detecting characteristics of a medium that is wholly or partly transparent, wherein said medium is placeable in an observation area in a light path extending between a light source and a light detector, wherein said medium is illuminated by the light source in the observation area, wherein at least one light-directing optical element is arranged in connection with the observation area, and wherein the light detector is adapted for determination of characteristics of said medium, wherein the detector is adapted to capture light transmitted only through said medium when the medium is in said observation area, the medium thus deflecting and changing direction of radiation of such light in the observation area;

wherein a processor is connected to the detector and configured to determine type of material, type of substance and/or a composition of types of materials or types of substances of said medium through spectrometry of said deflected light as received by the light detector, and wherein in the light path from the light source to the detector there is located at least one wavelength-selective element which is incorporated in or is arranged in association with the operation of the light source or the detector.

2. A device as disclosed in claim 1, further wherein a first optical element, which is optically focusing, is located at a first position in the light path, wherein a second optical element, which is optically focusing, is located at a second position in the light path between the first position and the detector, wherein the observation area is located between said first and second optical elements, wherein the first optical element receives light from the light source and is configured to direct that light towards the second element, wherein light from said second optical element is directed towards the light detector, wherein the light source is a light source having a dark center, wherein the light source and the first optical element provide light into an intermediate region between the first optical element and the second element within a specific angular spread spectrum which does not include forward direction as parallel light, wherein the second optical element is configured to focus light from the intermediate region towards an image plane in order to thereat a) to create an image of the light source and its dark centre, and b) to focus light which is scattered by said medium in a forward direction as parallel light towards the second optical element to a light detection field represented by said dark centre, and wherein said light detector is located in said light detection field.

3. A device as disclosed in claim 2, wherein a first optical element, which is light reflecting, is placed at a first position in the light path, wherein the first light reflecting element receives light from a light source that has a dark centre and directs this light on towards the light detector, wherein both the light source and the first optical element provide light in an intermediate area between the first optical element and the light detector within a specific angularly dispersed spectrum without light from the dark centre;

wherein the first optical element is arranged to reflect light towards an image plane located in the same or roughly the same plane as the light source in order to generate an image of the light source with its dark centre; and wherein the light detector is placed in said image plane coaxial with the dark centre of the light source in such manner that at least a part of the light that is scattered by said medium towards said dark centre will reach a light detection field represented by said dark centre, said light detector being located in the light detection field.

4. A device as disclosed in claim 3, wherein the light source with a dark centre is selected from the group consisting of:

an annular light source;

a polygonal light source;

a light source with a pair of parallel light lines;

at least two light sources arranged as a frame or ring around said dark centre;

a light source with reflector, diffuser and dark centre.

5. A device as disclosed in claim 1, further wherein a first optical element forms said at least one optical element and is located at a first position in the light path and configured to receive light from the light source having a dark centre and to direct said light further in a direction back towards the light source, the light source and the first optical element thereby both providing light into an intermediate region between the first optical element and the light detector, wherein the first optical element is configured to direct light towards an image plane located in the same or approximately the same plane as the light source to create an image of the light source with its dark centre, and wherein the light detector is located in said image plane coaxially with the dark center of the light source in such a manner that at least a portion of the light spread by said medium in a forward direction as parallel light will reach a light detection field represented by said dark centre, and said light detector being located in said light detection field.

6. A device as disclosed in claim 5,
wherein the first optical element is curved and focusing, or is a reflective, planar face.

7. A device according to claim 5, wherein the light provided into the intermediate region from the light source and the first optical element is within a specific angular spread spectrum which does not include forward direction as parallel light.

8. A device as disclosed in claim 1, wherein the light source is selected from the group consisting of a tunable laser and a modulatable light-emitting diode.

9. A device as disclosed in claim 1,
wherein said medium is surrounded by a fluid in the observation area;
and wherein said fluid has characteristic light deflecting properties that are different from the light deflecting properties of the said medium.

10. A device as disclosed in claim 1,
wherein in the light path from the light source to the detector, the observation area is located before a first occurrence of said at least one optical element.

11. A device as disclosed in claim 1,
wherein in the light path from the light source to the detector, the observation area is located after a first occurrence of the said at least one optical element.

12. A device as disclosed in claim 1,
wherein a first optical element, which is optically focusing, is located at a first position in the light path, that a second optical element, which is optically focusing, is located at a second position in the light path between the first position and the detector,
wherein the first optical element receives light from a light source and directs it on towards the second element; and
wherein light from said second optical element is directed towards the light detector.

13. A device as disclosed in claim 12,
wherein the light which is directed from the first optical element towards the second optical element is parallel light.

14. A device as disclosed in claim 12,
wherein in a first optical path length between the second optical element and the detector there is located a light stop to stop light that has not changed direction on passing through said observation area and which is focused towards the light stop; and
wherein in a second optical path length located between the light stop and the detector there is arranged a converging lens for focusing light that is deflected by said medium in said observation area and thus changes direction, and which is then led out from the second optical element and passes outside the periphery of the light stop towards the converging lens.

15. A device as disclosed in claim 12,
wherein in the light path from the light source to the detector, the observation area is located before or after a first occurrence of the said at least one optical element, and wherein the first focusing optical element represents said first occurrence of said at least one optical element.

16. A device as disclosed in claim 12,
wherein the light source is selected from the group consisting of:
a point light source,
a point light source provided by passing light through a diaphragm aperture, and
a light source with a dark centre provided by one of:
an annular light source;
a polygonal light source;
a light source with a pair of parallel light lines;
at least two light sources arranged as a frame or ring around said dark centre; and
a reflector-based light source with diffuser and dark centre.

17. A device according to claim 12,
wherein in an optical path area between the first optical element and the second optical element there is located a first raster or chequerboard-like filter for filtering away part of the parallel light coming from the first optical element;
wherein in the optical path at the exit from said optical path area there is located a second raster or chequerboard-like filter which is offset relative to the first filter so that parallel light which is allowed through by the first filter and is not deflected by said medium when it is located in said optical path area, is stopped by the second filter;
wherein the second optical element is arranged to capture light that has been received by said medium and deflected out therefrom towards and through the second filter; and
wherein the detector is arranged to capture said deflected light which comes focused from the second element towards the light detector.

18. A device as disclosed in claim 1,
wherein the light source is a light source with a dark centre;
wherein the light source and the first optical element provide light in an intermediate area or observation area between the first optical element and the second element within a specific angularly dispersed spectrum which does not include the forward direction as parallel light;
wherein the second optical element is arranged to focus light from the intermediate area or the observation area towards an image plane in order, on the plane,
a) to generate an image of the light source with its dark centre; and
b) to focus light that is scattered by said medium in a forward direction as parallel light towards the second optical element into a light detection field represented by said dark centre;
and wherein said light detector is located in the light detection field.

19. A device as disclosed in claim 18,
wherein the light source with the dark centre is selected from the group consisting of:
an annular light source;
a polygonal light source;
a light source with a pair of parallel light lines;
at least two light sources arranged as a frame or ring around said dark centre;
a reflector-based light source with diffuser and dark centre.

20. A device as disclosed in claim 1,
wherein light is directed towards the first optical element from a point light source and is directed on from the first optical element towards a focusing point;

wherein in an optical path area close to the focusing point there is located a light stop adapted to stop that of the point light source generated light which has not changed direction on passing through the observation area and which is focused towards the light stop;

wherein the light detector is placed behind or around the light stop for detecting the light which is deflected by said medium in the detection area and changes direction.

21. A device as disclosed in claim 1, wherein a first focusing optical element is located at a first position in the light path; and that the first optical element receives light from a light source which has a dark centre and directs this light on towards the light detector.

22. A device as disclosed in claim 21, wherein a second focusing optical element is located at a second position in the light path between the first position and the light detector;

wherein the first optical element receives light from the light source and directs it on towards the second optical element; and wherein light from said second optical element is directed towards the light detector.

23. A device as disclosed in claim 22, wherein the light source via the first optical element provides light in an intermediate area or observation area between the first optical element and the second optical element;

that the second optical element is arranged to focus light from the intermediate area towards an image plane in order, on the plane, a) to generate an image of the light source with its dark centre; and b) to focus light transmitted through said medium which is deflected by said medium towards the second optical element into a light detection field represented by said dark centre;

and wherein said light detector is located in the light detection field.

24. A device as disclosed in claim 21, wherein both the light source and the first optical element provide light in an intermediate area or observation area between the first optical element and the light detector within a specific angularly dispersed spectrum which does not include the forward direction as parallel light;

wherein the first optical element is arranged to focus light towards an image plane located in the same or roughly the same plane as the light source in order to generate an image of the light source with its dark centre;

and wherein the light detector is placed in said image plane coaxial with the dark centre of the light source, in such manner that at least a part of the light that is scattered by said medium in a forward direction as parallel light will reach a light detection field represented by said dark centre, said light detector being located in the light detection field.

25. A device as disclosed in claim 21, wherein the light source with dark centre is selected from the group consisting of:

an annular light source;

a polygonal light source;

a light source with a pair of parallel light lines;

at least two light sources arranged as a frame or ring around said dark centre.

26. A device as disclosed in claim 21, wherein the first focusing optical element is selected from the group consisting of:

a spherical reflector, an ellipsoid reflector, an element with aspherical shape, an element with a paraboloid shape, and an element with a hyperboloid shape.

27. A device as disclosed in claim 1, wherein the wavelength-selective element is designed for operation in the infrared or near-infrared (NIR) spectral range.

28. A device as disclosed in claim 1, wherein the detector includes an optical diffractive element with an entrance aperture to the detector configured to cause imaging on the diffractive element of at least a substantial part of the observation area.

29. A device as disclosed in claim 1, wherein a light mixer or light diffuser is arranged in connection with the light detector.

30. A device as disclosed in claim 1, wherein said first optical element is formed of a single or double curved mirror.

31. A device as disclosed in claim 1, wherein at least one of said first and second optical elements is formed of a single or double curved mirror.

32. A device as disclosed in claim 1, wherein said first optical element is formed as a lens or a lens segment.

33. A device as disclosed in claim 1, wherein at least one of said first and second optical elements is formed as lens or a lens segment.

34. A device as disclosed in claim 1, wherein at least one mirror element is positioned in the light path between the light source and the detector for redirecting the light path.

35. A device as disclosed in claim 34, wherein the mirror element is positioned in the light path between the light source and the first optical focusing element.

36. A device as disclosed in claim 1, wherein the device is adapted to detect a medium selected from the group consisting of:

a liquid medium, a solid medium of glass material, a solid medium of plastic material, an empty packaging made of glass material, and an empty packaging made of plastic material.

37. A device as disclosed in claim 1, wherein a first optical element, which is light reflecting, is placed at a first position in the light path; and wherein the first light reflecting element receives light from a light source that has a dark centre and directs this light on towards the light detector.

38. A device as disclosed in claim 1, wherein the first optical element is formed of a retro-reflector or a reflective fabric.

39. A device as disclosed in claim 1, wherein the detector is connected to a processor; and wherein connected to the processor in addition is at least one of: a device for weighing said medium, a camera for observing the detection area of the device, and a metal detector.

40. A device as disclosed in claim 1, wherein the light detector is connected to a spectrometer, that a camera is arranged for observing at least one detection area belonging to the device, that the camera is placed adjacent to the light detector, and that an extra light source is placed adjacent to the camera for illuminating said medium, e.g., an article, from above, the camera being arranged to view said medium from the side and/or from the top.

41. A device as disclosed in claim 40, wherein the camera is arranged to view two mutually separable detection areas from above and from the side, the camera and the extra light source being arranged above the junction between the two detection areas at a side edge of the areas.

42. A method for detecting characteristic features of a medium that is wholly or partly transparent, wherein said medium is placeable in an observation area in a light path extending between a light source and a light detector, wherein said medium is illuminated by the light source in the observation area, wherein at least one light-directing optical element is arranged in connection with the observation area, and wherein the light detector is adapted for determination of characteristics of said medium, the method further comprising:

detecting only light transmitted through said medium which is deflected by said medium when it is in said area and thus causes a change of direction in said area;

determining the characteristics in the form of type of material, type of substance and/or composition of types of materials or types of substances of said medium by spectrometry of the deflected light received by the light detector; and using a wavelength-selective element at a position in the light path, the element functioning being included in or arranged in association with the operation of the light source or the detector.

43. A method as disclosed in claim 42, wherein said medium is introduced into an area surrounded by a fluid, said fluid having characteristic light deflecting properties that are different from the light deflecting properties of the said medium.

44. A method as disclosed in claim 42, further comprising:

generating the light from a source and directing it via a first optical focusing element on to a second focusing optical element that is located at a position which, in a nominal light path, is between the first optical element and the light detector; and directing light out from said second optical element towards the light detector.

45. A method as disclosed in claim 44, further comprising:

directing the light from the first optical element towards the second element as parallel light.

46. A method as disclosed in claim 44, further comprising:

stopping light which has not changed direction on passing through the observation area and which is focused towards a light stop, said stopping being effected in an optical path length between the second optical focusing element and the detector; and focusing towards the detector the light which is deflected by said medium in said observation area and thus changes direction, which is led out from the second optical focusing element, and which then passes outside the periphery of the light stop.

47. A method as disclosed in claim 46, further comprising:

focusing towards the detector with the aid of a converging lens the light that is deflected by said medium in said observation area and thus changes direction, which is led out from the second optical element and which then passes outside the periphery of the light stop towards the detector, the converging lens being used in a second optical path length located between the light stop and the light detector.

48. A method as disclosed in claim 44,
wherein the light is generated from a point light source.

49. A method as disclosed in claim 42,
wherein focusing of the light is carried out at a position which, in a nominal light path, is between the first element and the detector.

50. A method as disclosed in claim 49, further comprising:

providing light from a light source with a dark centre in said area within a specific angularly dispersed spectrum which does not include the forward direction as parallel light;

focusing light from the area towards an image plane in order to generate on the plane an image of the light source with its dark centre; and focusing light that is deflected by said medium in a forward direction as parallel light towards the second optical focusing element into a light detection field represented by said dark centre.

51. A method as disclosed in claim 42, further comprising:

in an optical path between the first optical focusing element and said observation area, filtering away by means of a first filtering part of the parallel light coming from the first optical element;

in the optical path at the exit from said observation area, causing parallel light that is allowed through by the first filtering and is not deflected by said medium in said observation area to be stopped by the second filtering;

capturing light that has been received by said medium and deflected out therefrom and thus has not been stopped by the second filtering; and capturing said deflected light which comes focused from the second optical focusing element towards the light detector.

52. A method as disclosed in claim 51, wherein a point light source is used as the light source.

53. A method as disclosed in claim 42, further comprising:

directing light towards the first optical focusing element from a point light source and then from the first element towards a focusing point;

in an optical path area close to the focusing point, stopping that of the point light source generated light which has not changed direction on passing through said observation area and which is focused towards the focusing point; and in a position behind or surrounding the focusing point, detecting the light which is deflected by said medium in said observation area and thus changes direction.

54. A method as disclosed claim 42, further comprising:

allowing light from a light source with a dark centre to be directed via a first focusing optical element located at a first position in the light path towards the light detector.

55. A method as disclosed in claim 54, further comprising:

allowing the light from the light source to be directed via the first optical focusing element towards a second optical focusing element which is located at a second position in the light path between the first position and the light detector.

56. A method as disclosed in claim 55, further comprising:

providing light in an observation area between the first optical focusing element and the light detector within a specific angularly dispersed spectrum which does not include the forward direction as parallel light;

allowing the second optical element to focus light from the observation area towards an image plane;

generating on the image plane an image of the light source with its dark centre; and focusing light that is deflected by said medium in a forward direction as parallel light towards the second optical focusing element into a light detection field represented by said dark centre.

57. A method as disclosed in claim 54, further comprising:
allowing light to be provided in an observation area between the first optical focusing element and the light detector within a specific angularly dispersed spectrum which does not include the forward direction as parallel light;
by means of the first optical focusing element, focusing light towards an image plane in order to generate an image of the light source with its dark centre; and
allowing at least a part of the light that is scattered by said medium in a forward direction as parallel light to reach a light detection field represented by said dark centre.

58. A method as disclosed in claim 54,
wherein the light source which has a dark centre is configured as one of:
an annular light source;
a polygonal light source;
a light source with a pair of parallel light lines;
at least two light sources arranged as a frame or ring around said dark centre:
a light source with reflector, diffuser and dark centre.

59. A method as disclosed in claim 54, wherein the first focusing optical element is configured as one of:
a spherical reflector, an ellipsoid reflector, an element of aspherical shape, an element of paraboloid shape, and an element of hyperboloid shape.

60. A method as disclosed in claim 42,
wherein light detection spectrometry is of NIR type.

61. A method as disclosed in claim 42,
wherein the light source and the light detector operate in the infrared or near-infrared spectral range.

62. A method as disclosed in claim 42,
wherein a single or double curved mirror is used as said first optical focusing element or at least one of said first and second optical focusing elements.

63. A method as disclosed in claim 42, a lens or a lens segment is used as said first element or at least one of said first and second elements.

64. A method as disclosed in claim 42, at least one light path redirecting mirror element is placed in the light path between the light source and the detector.

65. A method as disclosed in claim 64, wherein said mirror element is tilted relative to the incident light path direction.

66. A method as disclosed in claim 42,
wherein said medium passing through the detection area is presented therein as a liquid material or as a solid material of glass or plastic.

67. A method as disclosed in claim 42, further comprising:
locating a first light reflecting element at a first position in the light path to receive light from a light source which has a dark centre and directing this light on towards the light detector.

68. A method as disclosed in claim 67, further comprising:
providing light in an intermediate area between the light source and the first element within a specific angularly dispersed spectrum without light from the dark centre;
reflecting light towards an image plane located in the same or roughly the same plane as the light source in order to generate an image of the light source with its dark centre; and
causing at least a part of the light that is scattered by said medium towards the dark centre to reach a light detection field represented by said dark centre.

69. A method as disclosed in claim 68,
wherein said medium passing through the detection area is presented therein as a liquid material or as a solid material of glass or plastic.

70. A method as disclosed in claim 67,
wherein the light is reflected using retro-reflection or dispersive reflection.

71. A method as disclosed in claim 67,
wherein the light source which has a dark centre is configured as one of:
an annular light source;
a polygonal light source;
a light source with a pair of parallel light lines;
at least two light sources arranged as a frame or ring around said dark centre:
a light source with reflector, diffuser and dark centre.

72. A method as disclosed in claim 67,
wherein the light source and the light detector operate in the infrared or near-infrared spectral range.

73. A method as disclosed in claim 42,
wherein output from the detector is processed by a processor, and wherein said processing further comprises processing signals derived from subjecting said medium to at least one of the following operations:
weighing, camera-based observation and metal detection.

74. A method as disclosed in claim 42, further comprising:
viewing said medium through camera observation from the side and/or from above, either in one observation area or in two mutually separable observations areas.

75. A method as disclosed in claim 74, further comprising:
coordinating the camera observation with signal output from the light detector connected to a spectrometer in order to determine at least one of the following parameters:
area of said medium;
material colour of transparent medium;
material colour of non-transparent medium;
shape of said medium;
movements of said medium.

76. A method as disclosed in claim 74,
wherein the camera observation includes controlling operative states in at least one observation area.

* * * * *